United States Patent
Jones

(10) Patent No.: US 8,195,848 B2
(45) Date of Patent: Jun. 5, 2012

(54) MEDICAL DEVICE CREATED THROUGH RESOURCE LEVERAGE OF A HOST PROCESSING SYSTEM AND METHOD

(75) Inventor: Zach Jones, Half Moon Bay, CA (US)

(73) Assignee: EconoMEDics, Inc., Palo Alto, CA (US)

( * ) Notice: Subject to any disclaimer, the term of this patent is extended or adjusted under 35 U.S.C. 154(b) by 643 days.

(21) Appl. No.: 12/062,541

(22) Filed: Apr. 4, 2008

(65) Prior Publication Data
US 2009/0254681 A1 Oct. 8, 2009

(51) Int. Cl.
*G06F 3/00* (2006.01)

(52) U.S. Cl. ......................................................... 710/38
(58) Field of Classification Search ....................... 710/38
See application file for complete search history.

(56) References Cited

U.S. PATENT DOCUMENTS

| | | | |
|---|---|---|---|
| 5,876,351 A | 3/1999 | Rohde | |
| 6,074,345 A | 6/2000 | Van Oostrom et al. | |
| 6,112,224 A * | 8/2000 | Peifer et al. | 709/202 |
| 6,364,834 B1 | 4/2002 | Reuss et al. | |
| 6,547,730 B1 | 4/2003 | Lin et al. | |
| 6,558,320 B1 | 5/2003 | Causey, III et al. | |
| 6,730,025 B1 * | 5/2004 | Platt | 600/300 |
| 6,754,725 B1 * | 6/2004 | Wright et al. | 710/8 |
| 7,162,306 B2 | 1/2007 | Caby et al. | |
| 7,249,036 B2 | 7/2007 | Bayne | |
| 7,330,763 B1 | 2/2008 | Cullen et al. | |
| 7,356,740 B2 | 4/2008 | Neumiller et al. | |
| 2002/0184055 A1 * | 12/2002 | Naghavi et al. | 705/2 |
| 2006/0282654 A1 * | 12/2006 | Veen et al. | 713/1 |
| 2008/0209199 A1 * | 8/2008 | Sadovsky et al. | 713/2 |

* cited by examiner

*Primary Examiner* — Henry Tsai
*Assistant Examiner* — Eric Oberly
(74) *Attorney, Agent, or Firm* — Kilpatrick Townsend and Stockton LLP

(57) ABSTRACT

A method, system, and apparatus of medical device created through resource leverage of a host processing system are disclosed. In one embodiment, a method of a medical component includes automatically communicating a medical operating system to a host processing system from a memory location of the medical component when it is determined that the host processing system does not include a medical operating system optimized to operate with the medical component, processing a confirmation from the host processing system that the medial operating system has repurposed the host processing system of the host processor and that the medical operating system is now active on the host processing system, capturing a patient reading through the medical component, and leveraging at least one of a processing resource and an input-output (I/O) resource of the host processing system in providing a measurement of the patient reading to a user.

16 Claims, 9 Drawing Sheets

| PATIENT ID 302 | MEDICAL COMPONENT CONNECTED 304 | BLOOD PRESSURE 306 | SUGAR LEVEL IN BLOOD 308 | PULSE RATE/ HEART CONDITION 310 | TEMPERATURE 312 | OXYGEN LEVEL IN BLOOD 314 |
|---|---|---|---|---|---|---|
| APS11625 | BLOOD PRESSURE AND PULSE READER | 100/80 mm/Hg | NA | 80 BPM | NA | NA |
| BBA87232 | ECG | NA | 95 mg/dl | NORMAL | NA | NA |
| K2D34654 | PULSE OXIMETER AND GLUCOSE METER | NA | NA | NA | NA | HIGH |
| JDS03874 | PULSE RATE WATCH DIGITAL THERMOMETER | NA | NA | 75 BPM | 90°F | NA |
| • • • | • • • | • • • | • • • | • • • | • • • | • • • |

TABLE VIEW 350

FIGURE 3

MEDICAL DEVICE CREATED THROUGH RESOURCE LEVERAGE OF A HOST PROCESSING SYSTEM AND METHOD

FIELD OF TECHNOLOGY

This disclosure relates generally to an enterprise method, a technical field of software and/or hardware technology and, in one example embodiment, to a medical device created through resource leverage of a host processing system and method.

BACKGROUND

A medical device (e.g., a pulse oximeter, an electrocardiograph, etc.) may require a data processing capability to operate (e.g., processing power, random access memory, non-volatile memory, and input/output resources, etc.). For example, the medical device may require a processor to analyze measurements, a memory to store data, a display to show data, a keyboard to receive input commands, and/or a printer to output readings.

A manufacturer of the medical device may include the data processing capability integrated into the medical device. Sometimes, the manufacturer may create interfaces between the medical device and customized data processing systems designed for the medical device. By including the data processing capability with the medical device, costs of the medical device may increase. Furthermore, when the medical device is no longer used (e.g., obsolete, component broken, etc.), the data processing capability of the medical device may be wasted (e.g., because the data processing capability may be designed for and/or integrated with the medical device).

An organization (e.g., a company, a non-profit agency, a government, etc.) may provide (e.g., sell, donate, etc.) an application-optimized data processing system (e.g., a One-Laptop-Per-Child computer, an Intel® Classmate PC®, an ASUS Eee PC®, etc.) to individuals in need (e.g., children in a developing country). To save costs and resources, the application-optimized data processing system may include hardware components (e.g., a microprocessor, memory, a display, I/O devices, etc.) and software (e.g., an operating system) that are optimized for a particular type of application (e.g., word processing, education, etc.).

The operating system of the application-optimized data processing system may be developed for non-medical applications. In addition, the operating system of the application-optimized data processing system may not be reliable (e.g., may be susceptible to freezing, may perform functions not required for medical purposes, etc.).

SUMMARY

A method, system, and apparatus of medical device created through resource leverage of a host processing system are disclosed. In one aspect, a method of a medical component includes automatically communicating a medical operating system to a host processing system from a memory location of the medical component when it may be determined that the host processing system does not include a medical operating system optimized to operate with the medical component, processing a confirmation from the host processing system that the medial operating system has repurposed the host processing system of the host processor and that the medical operating system may be now active on the host processing system, capturing a patient reading through the medical component, and leveraging any one of a processing resource and an input-output (I/O) resource of the host processing system in providing a measurement of the patient reading to a user.

The method may include automatically communicating an application to the host processing system from a different memory location of the medical component (e.g., when confirmed that the medical operating system is active on the host processing system). The method may also include determining that the host processing system already includes a certain medical operating system is optimized to operate with another medical component. The method may communicate application and/or operating system data that may update the certain operating system to be equivalent to the medical operating system.

The patient reading may be an electrocardiogram that records an electrical activity of a heart of a patient over time. The patient reading may be a photoplethysmograph of a pulse oximeter that may indirectly measure the oxygen saturation of blood of a patient and changes in blood volume in a skin of the patient. The medical operating system may be common to the medical component and other medical components (e.g., when other medical components may be coupled with the host processing system, the medical operating system of the host processing system does not need to be reinstalled).

The method may further include leveraging a power supply of the host processing system to power the medical component. The medical component may be coupled with the host processing system through a standard interface (e.g., the standard interface may be a Universal Serial Bus (USB) interface). The processing resource may be a microprocessor of the host processing system. The I/O resource of the host processing system may be a printing device, a display device, an input device, and/or a network communication resource.

In addition, the method may include using a signal processor of the medical component to process a complex data when the patient reading through the medical component requires processing capability that cannot be supplied from the host processing system.

In another aspect, a method of a host processing system includes automatically repurposing the host processing system with a medical operating system communicated from a memory location of a medical component when it is determined that the medical operating system is optimized to operate with the host processing system and the medical component, activating the medical operating system on the host processing system such that the medical operating system takes precedence over the original operating system in a boot process of the host processing system when the medical component is coupled with the host processing system, processing a patient reading captured through the medical component using a processor module of the host processing system, and generating a measurement of the patient reading using the processor module of the host processing system and an application of the medical operating system.

The method may include automatically receiving the application of the medical operating system from a different memory location of the medical component (e.g., when it may be confirmed that the medical operating system may have repurposed the host processing system to operate the medical component). The method may further include determining that another medical component may be coupled with the host processing system. The method may also include applying an update code received from the another medical component to update the medical operating system to be compatible with the another medical component.

The method may execute another application of the another medical component using the host processor from the another medical component and/or the host processing system. The medical operating system of the host processing system may not need to be reinstalled even when other medical components are coupled with the host processing system.

In yet another aspect, a system includes a medical component to capture a patient reading and to provide a medical operating system optimized for the medical component, and a host processing system to couple with the medical component through a standard interface of the host processing system, and to replace an original operating system of the host processing system with that of the medical operating system when the medical component is coupled with the host processing system.

The medical operating system may be shared among medical components each providing a different patient reading to the host processing system. The standard interface may be a Universal Serial Bus (USB) interface. The medical component may be a self-powered medical component that may have independent imaging, I/O, and processing capability that may pre-process a data associated with a patient prior to communicating the data to the host processing system.

The methods, systems, and apparatuses disclosed herein may be implemented in any means for achieving various aspects, and may be executed in a form of a machine-readable medium embodying a set of instructions that, when executed by a machine, cause the machine to perform any of the operations disclosed herein. Other features will be apparent from the accompanying drawings and from the detailed description that follows.

BRIEF DESCRIPTION OF THE DRAWINGS

Example embodiments are illustrated by way of example and not limitation in the figures of the accompanying drawings, in which like references indicate similar elements and in which:

FIG. 3 is a table view of medical devices connected to host processing system displaying the diagnosed readings associated with a patient having a particular patient ID, according to one embodiment.

Other features of the present embodiments will be apparent from the accompanying drawings and from the detailed description that follows.

DETAILED DESCRIPTION

A method, system, and apparatus of medical device created through resource leverage of a host processing system are disclosed. Although the present embodiments have been described with reference to specific example embodiments, it will be evident that various modifications and changes may be made to these embodiments without departing from the broader spirit and scope of the various embodiments.

Figure 1:
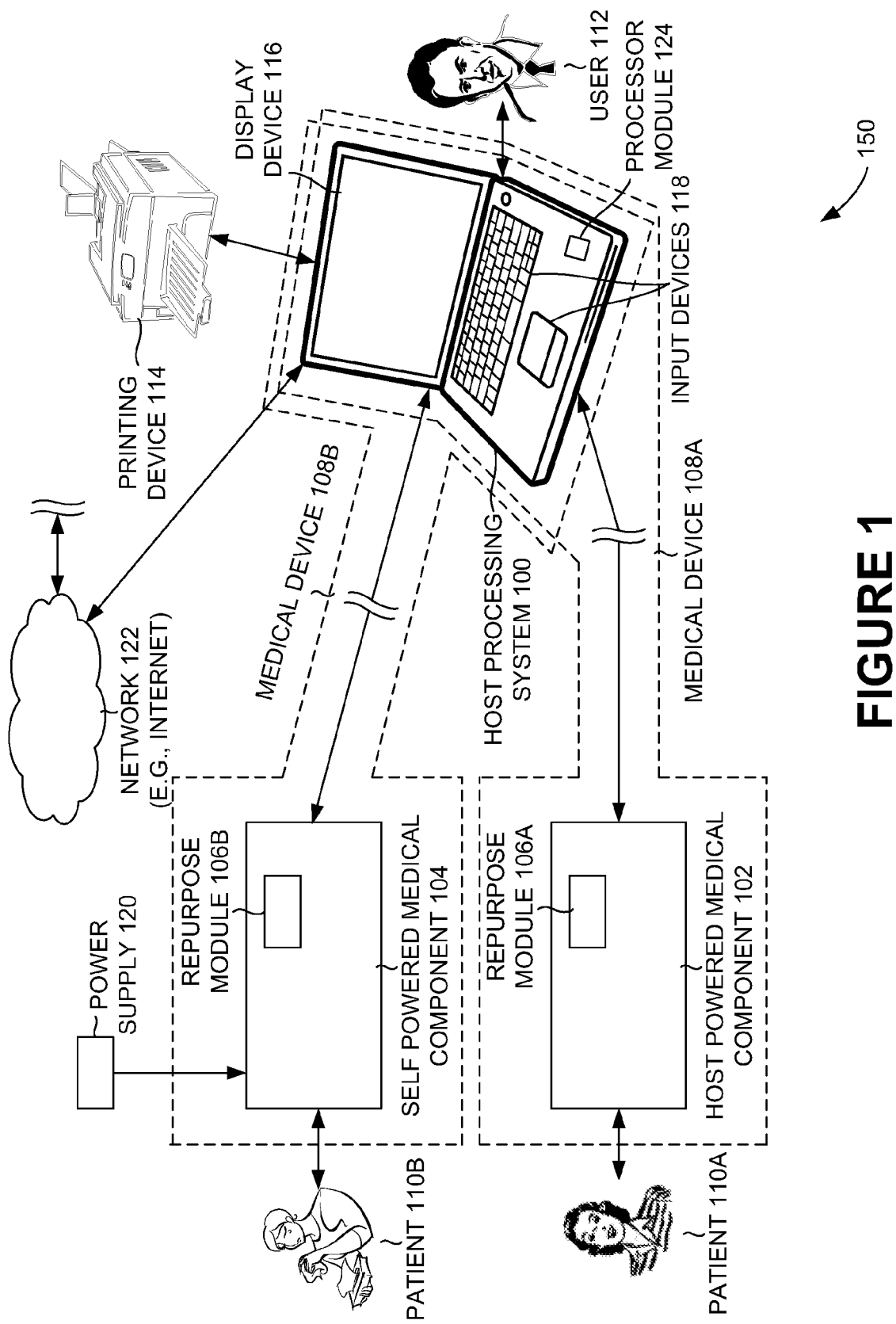
FIG. 1 is a system view of a user communicating with a host processing system to process a patient reading through a medical component, according to one embodiment.

In one embodiment, a method of a medical component includes automatically communicating a medical operating system to a host processing system (e.g., the host processing system 100 of FIG. 1) from a memory location of the medical component (e.g., memory device 210 of FIG. 2) when it is determined that the host processing system 100 does not include a medical operating system optimized to operate with the medical component (e.g., host powered medical component 102 and/or self powered medical component 104 of FIG. 1), processing a confirmation (e.g., acknowledgement) from the host processing system 100 that the medial operating system has repurposed the host processing system of the host processor and that the medical operating system (e.g., of the operating system module 206) is now active on the host processing system 100, capturing a patient reading (e.g., the patient reading 404 of FIG. 4) through the medical component (e.g., host powered medical component 102 and/or self powered medical component 104 of FIG. 1), and leveraging a processing resource and/or an input-output (I/O) resource (e.g., printer, ECG printer, etc.) of the host processing system 100 in providing a measurement of the patient reading 404 to a user (e.g., the user 112 of FIG. 1).

In another embodiment, a method of a host processing system (e.g., the host processing system 100 of FIG. 1) includes automatically repurposing the host processing system 100 with a medical operating system (e.g., of the operating system module 206) communicated from a memory device 210 of a medical component (e.g., host powered medical component 102 and/or self powered medical component 104 of FIG. 1) when it is determined that the medical operating system (e.g., of the operating system module 206) is optimized to operate with the host processing system 100 and the medical component (e.g., host powered medical component 102 and/or self powered medical component 104 of FIG. 1), activating the medical operating system (e.g., of the operating system module 206) on the host processing system 100 such that the medical operating system (e.g., of the operating system module 206) takes precedence over the original operating system in a boot process of the host processing system 100 when the medical component (e.g., host powered medical component 102 and/or self powered medical component 104 of FIG. 1) is coupled with the host processing system 100, processing a patient reading (e.g., the patient reading 404 of FIG. 4) captured through the medical component (e.g., host powered medical component 102 and/or self powered medical component 104 of FIG. 1) using a processor module (e.g., the processor module 204 of FIG. 2) of the host processing system 100, and generating a measurement of the patient reading 404 using the processor module 204 of the host processing system 100 and an application of the medical operating system (e.g., host powered medical component 102 and/or self powered medical component 104 of FIG. 1).

Figure 4:
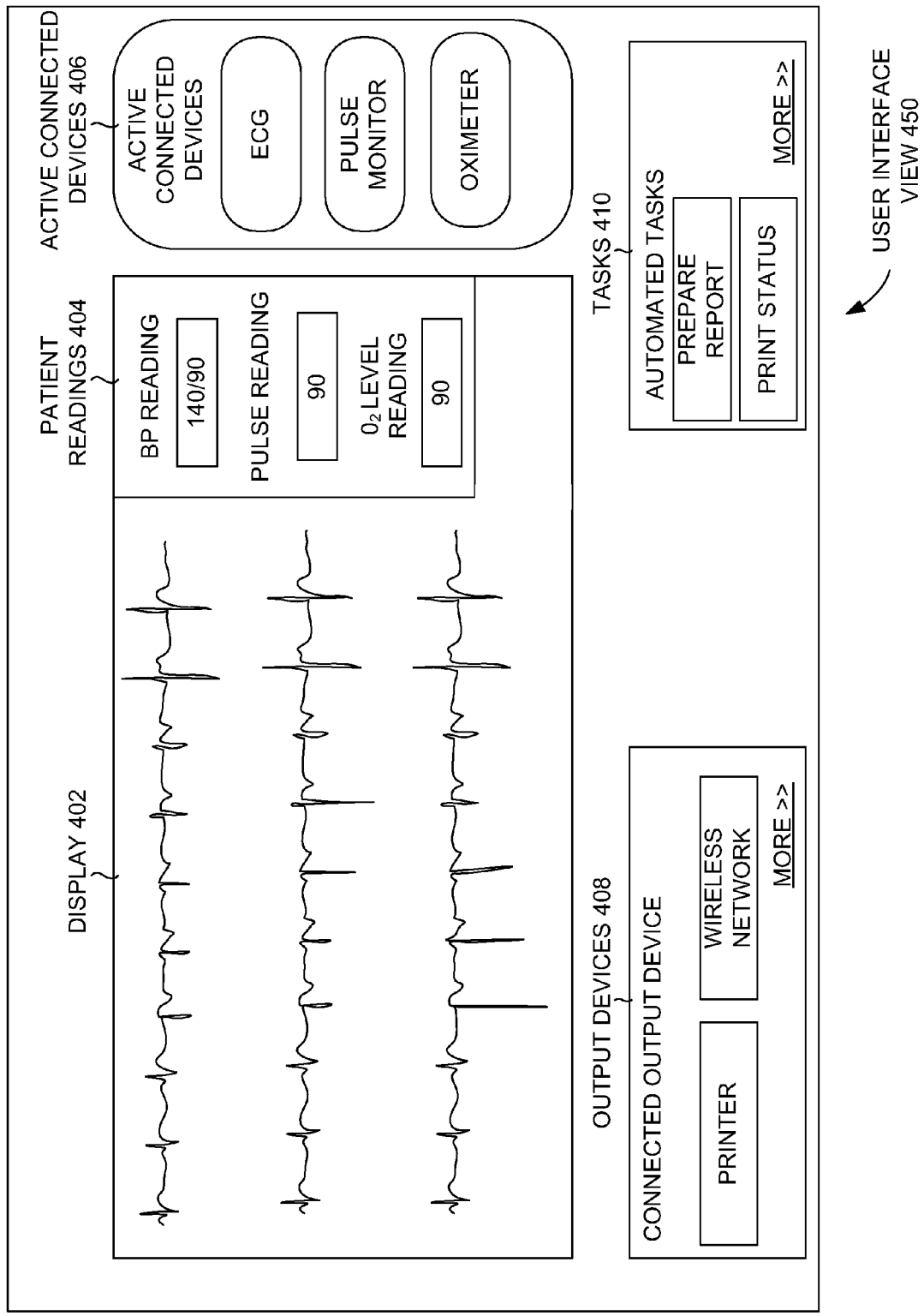
FIG. 4 is a user interface view of an illustrating a medical device operating system running on a host processing system with other applications optimized for a medical device, according to one embodiment.

In yet another embodiment, a system includes a medical component (e.g., host powered medical component 102 and/ or self powered medical component 104 of FIG. 1) to capture a patient reading (e.g., the patient reading 404 of FIG. 4) and to provide a medical operating system (e.g., the medical operating system (e.g., of the operating system module 206) of FIG. 4) optimized for the medical component, and a host processing system (e.g., the host processing system 100 of FIG. 1) to couple with the medical component (e.g., host powered medical component 102 and/or self powered medical component 104 of FIG. 1) through a standard interface of the host processing system 100, and to replace an original operating system of the host processing system 100 with that of the medical operating system when the medical component is coupled with the host processing system 100.

FIG. 1 is a system view of a user 112 communicating with a host processing system 100 to process a patient (e.g., the patient 110A and 110B) reading through a medical component (e.g., the host powered medical component 102 and/or the self powered medical component 104), according to one embodiment. Particularly, FIG. 1 illustrates a host processing system 100, a host powered medical component 102, a self powered medical component 104, a repurpose module 106A, a repurpose module 106B, a medical device 108A, a medical device 108B, a patient 110A, a patient 110B, an user 112, a printing device 114, a display device 116, an input devices 118, a power supply 120, network 122, and a processor module 124, according to one embodiment.

The host processing system 100 may be processing device (e.g., a low cost computer, laptop, etc) which may communicate with the medical components through medical device for processing patient's data. The host powered medical component 102 may a medical component used to diagnose patients (e.g., the patients 110A and 110B of FIG. 1) and which is powered using a power supply of a host processing system (e.g., a standard interface port of the host processing system, etc.). The self powered medical component 104 may be a medical component used to diagnose patients (e.g., the patients 110A and 110B of FIG. 1) which may run using power supply 120. The repurpose module 106A of the host powered medical component 102 may communicate an operating system and/or other applications of the medical device 108A when necessary from a memory location of the medical component (e.g., the memory device 210 of FIG. 2) to the host processing system 100. The repurpose module 106B of the self powered medical component 104 may communicate an operating system and/or other applications of the medical component 108B when necessary from a memory location of the medical component (e.g., similar to the memory device 210 of FIG. 2) to the host processing system 100.

The medical device 108A may be a combination of the medical component 104 and the host processing system 100. The medical component 104 may be used to diagnose the patient 110A. Processing and other activities may be managed by the host processing system 100 by eliminating the extra processing complexity from the medical component 108A. The medical device 108B may be a combination of the medical component 104 and the host processing system 100 used to diagnose patient data. The patient 110A and 110B may be individuals who may require medical care or treatment. The user 112 (e.g., a doctor, a nurse, a skilled worker of the medical component, etc.) may be an individual who may use the host processing system for processing diagnostic data through the medical components (e.g., may include the host powered medical component 102 and/or the self powered medical component 104).

The printing device 114 may print the reports (e.g., readings, results, ECG report, etc). The display device 116 may display diagnostic information of the patient 110A-B (e.g., ECG readings, BP reading, etc. as illustrated in FIG. 4). The input devices 118 may be input devices associated with the host processing system 100 (e.g., key board, etc.). The power supply 120 may be a source of power supplying power (e.g., may be power line, battery, UPS, etc.) to the self powered medical component 104. The network 122 may be a local area network, a wide area network, an internet network, etc which may allow the host processing system to communicate with outside world (e.g., may include web updates, may be remote applications, etc.). The processor module 124 of the host processing system may process the patient reading (e.g., the patient reading 404 of FIG. 4) captured may be the medical component 102 and 104.

In example embodiment, the host processing system 100 may process the input diagnostic information of the patient 110A-B coming from the medical components 102 and 104 (e.g., ECG device, BP apparatus, oximeter, etc.) through the medical device 108A and 108B. The host processing system 100 may be controlled by the user 112 (e.g., a doctor, a skilled worker, etc.) and may have input/output devices connected to it (e.g., printer, etc.). The network 122 connection to the host processing system 100 may allow the host processing system 100 to communicate with the outside world (e.g., for updates, etc.).

In one embodiment, the medical operating system may be automatically communicated to a host processing system (e.g., the host processing system 100 of FIG. 1) from a memory location (e.g., the memory device 210 of FIG. 2) of the medical component (e.g., the self powered medical component 104 and/or host powered medical component 102) when it is determined that the host processing system 100 does not include a medical operating system optimized to operate with the medical component (e.g., the self powered medical component 104 and/or host powered medical component 102).

A confirmation may be processed from the host processing system 100 that the medial operating system has repurposed the host processing system 100 of the host processor (e.g., using the repurpose module 106A and 106B of FIG. 1) and that the medical operating system is now active on the host processing system 100. A patient reading (e.g., the patient reading 404 and other readings of FIG. 4) may be captured through the medical component (e.g., the self powered medical component 104 and/or host powered medical component 102). Any one of a processing resource and an input-output (I/O) resource of the host processing system 100 may be leveraged in providing a measurement of the patient reading 404 to the user 112.

The medical operating system may be common to the medical component (e.g., the host powered medical component 102 and/or the self powered medical component 104 of FIG. 1) and other medical components (e.g., the other medical components may be coupled with the host processing system 100, the medical operating system of the host processing system 100 does not need to be reinstalled). The power supply (e.g., the power supply 120 of FIG. 1) of the host processing system 100 may be leveraged to power the medical component (e.g., the host powered medical component 102 and/or the self powered medical component 104 of FIG. 1).

The medical component (e.g., the host powered medical component 102 and/or the self powered medical component 104 of FIG. 1) may be coupled with the host processing system 100 through a standard interface. The standard interface may be a Universal Serial Bus (USB) interface. The processing resource may be a microprocessor of the host processing system 100. The I/O resource of the host processing system 100 may be one of a printing device (e.g., the printing device 114 of FIG. 1), a display device (e.g., the display device 116 of FIG. 1), an input device (e.g., the input device 118 and other devices of FIG. 1), and/or a network communication resource.

A medical component (e.g. the host powered medical component 102 and the self powered medical component 104) may capture a patient reading (e.g., the patient reading 404 of FIG. 4) and may provide a medical operating system optimized for the medical component. The host processing system (e.g., the host processing system 100 of FIG. 1) may couple with the medical component through a standard interface (e.g., may be a Universal Serial Bus (USB) interface) of the host processing system 100, and may replace the host processing system 100 with that of the medical operating system when the medical component 102 and 104 is coupled with the host processing system 100.

Figure 2:
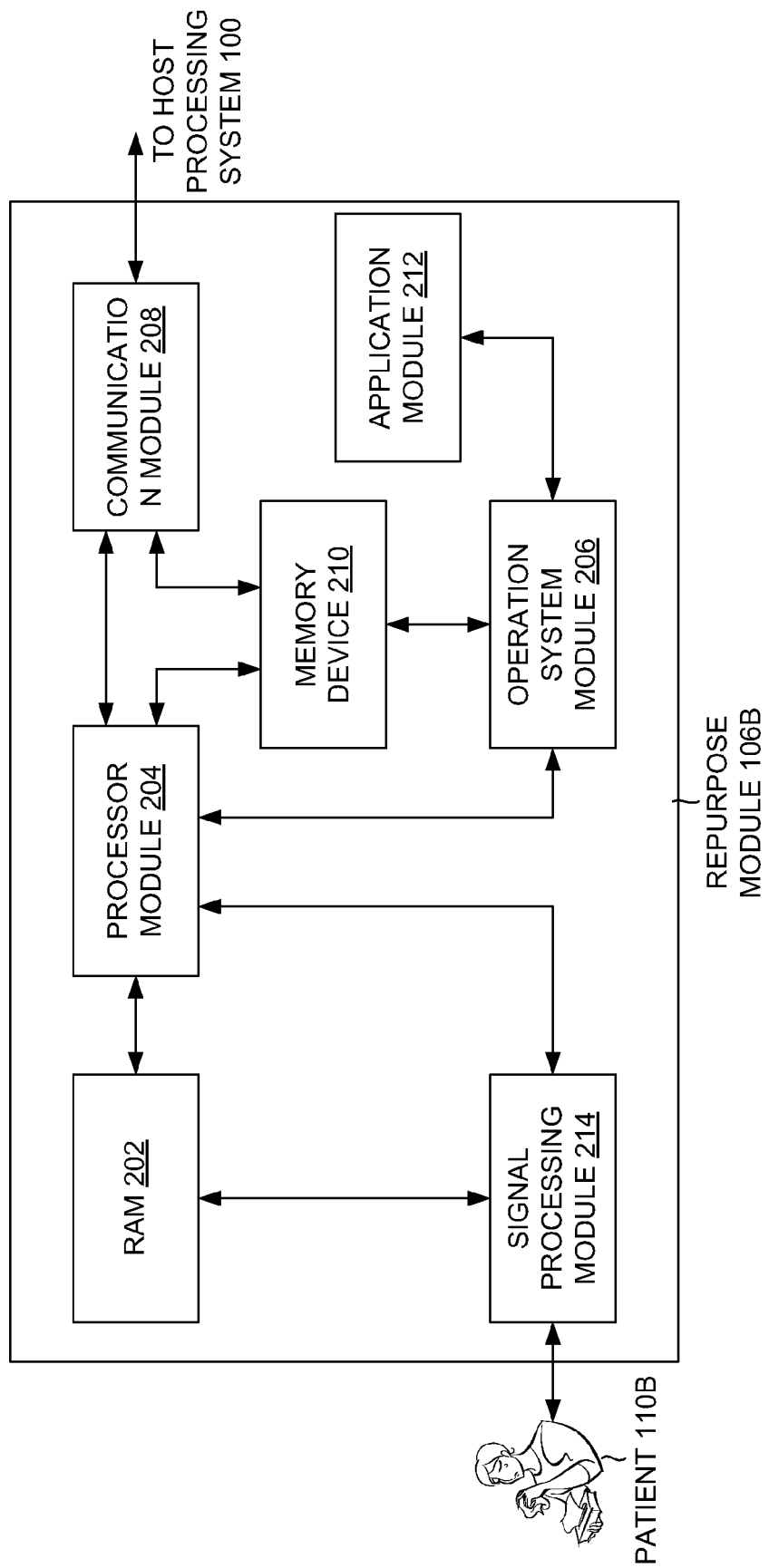
FIG. 2 is an exploded view of the repurpose module of FIG. 1, according to one embodiment.

FIG. 2 is an exploded view of the repurpose module of FIG. 1, according to one embodiment. Particularly, FIG. 2 illustrates a host processing system 100, a repurpose module 106A-B, a patient 110, a RAM 202, a processor module 204, an operating system module 206, a communication module 208, a memory device 210, an application module 212, and an signal processing module 214, according to one embodiment.

The RAM 202 may be a temporary storage memory for processing information (e.g., such as taking the diagnostic information, etc.) and communicating the diagnostic information to the processor module 204. The processor module 204 may process the diagnostic information from the RAM 202 and may send the information to the host processing system 100. The operating system module 206 may send the medical operating system to the host processing system 100 when the medical component 102 and 104 finds the operating system of the host processing system not optimized for the medical component 102 and 104. The communication module 208 may communicate information (e.g., the medical operating system, the patient's diagnostic readings, other applications necessary for the host processing system 100 etc.). The memory device 210 may store the information (e.g., diagnostic information, the operating system information, etc.). The application module 212 may include applications related to the medical components 102 (e.g., similarly for medical component 104) for diagnosing and processing the patients' readings. The applications may also be sent to the host processing system 100 when necessary. The signal processing module 214 may process a complex data when the patient reading through the medical component requires processing capability that cannot be supplied from the host processing system.

In example embodiment, the diagnostic information of the patient 110B may taken and processed by the processor module 204 through the signal processing module 214 and the diagnostic information may be communicated to the host processing system 100 through the communication module 208 which may also communicate the medical operating system (e.g., using the operating system module 206) to the host processing system 100.

In one embodiment, an application may be automatically communicated to the host processing system 100 from a different memory location of the medical component (e.g., using the communication module 208 of FIG. 2) when it may be confirmed that the medical operating system has the host processing system 100. It may be determined that the host processing system 100 already includes a certain medical operating system optimized to operate with another medical component (e.g., using the operating system module 206 of FIG. 2). Only the application and operating system data may be communicated that updates the certain operating system to be equivalent to the medical operating system (e.g., using the operating system module 206 of FIG. 2). The patient reading 404 may be an electrocardiogram that records an electrical activity of a heart of a patient over time. The patient reading 404 may be a photoplethysmograph of a pulse oximeter that may be indirectly measure the oxygen saturation of blood of the patient (e.g., the patient 110A-110B of FIG. 1) and changes in blood volume in a skin of the patient 110A-110B.

A signal processor of the medical component 102 and 104 may be used to process a complex data when the patient reading 404 through the medical component 102 and 104 requires processing capability that cannot be supplied from the host processing system 100 (e.g., using the processor module 204 of FIG. 2). The host processing system may be automatically repurposed with the medical operating system communicated from a memory location (e.g., the memory device 210 of FIG. 2) of the medical component when it may be determined that the medical operating system is optimized to operate with the host processing system 100 and the medical component (e.g., using the repurpose module 106A-B of FIG. 2).

The medical operating system may be activated on the host processing system 100 (e.g., the medical operating system takes precedence over the host processing system 100 in a boot process of the host processing system 100 when the medical component is coupled with the host processing system 100). A patient reading 404 captured may be processed through the medical component using a processor module (e.g., the processor module 204 of FIG. 2) of the host processing system 100. A measurement of the patient reading 404 may be generated using the processor module 204 of the host processing system 100 and an application of the medical operating system.

The application of the medical operating system may be received automatically from a different memory location of the medical component 102 and 104 when it may be confirmed that the medical operating system has repurposed the host processing system to operate with the medical component 102 and 104. It may be determined that another medical component is coupled with the host processing system 100. An update code received may be applied from the another medical component that may update the medical operating system to be compatible with the another medical component. Another application of the another medical component may be executed using the host processor from any one of the another medical component and the host processing system 100. The medical operating system of the host processing system 100 may not need to be reinstalled even when other medical components are coupled with the host processing system 100.

FIG. 3 is a table view 350 of the medical devices (e.g., the medical devices 108A and the medical devices 108B) connected to host processing system 100 displaying the diagnosed readings associated with a patient 110A-B having a particular patient ID, according to one embodiment. Particularly, FIG. 3 illustrates a patient ID field 302, a medical component connected 304, a blood pressure field 306, a sugar level field 308, a pulse rate/heart condition field 310, a temperature field 312 and an oxygen level in blood field 314, according to one embodiment.

The patient ID field 302 may be a field where unique patient ID associated to particular patient are represented. The medical component connected 304 may be a field where name of the medical devices connected to the system are represented. The blood pressure field 306 may be a field where blood pressure readings of the patient 110A-B are represented. The sugar level field 308 may be a field where readings of sugar level of blood of the patient 110A-B are represented. The pulse rate/heart condition 310 may be a field where pulse rate of the patient 110A-B are represented. The temperature field 312 may be a field of the patient 110A-B where temperature readings of the patient are represented. The oxygen level in blood 314 field may be a field where the report of the oxygen level in blood the patient 110A-B is represented.

In example embodiment, the patient ID field 302 may illustrate a patient ID APS11625, a patient ID BBA87232, a patient ID K2D34654 and a patient ID JDS03874. The medical component connected 304 field may illustrate a blood pressure and pulse reader, an ECG, a pulse oximeter and glucose meter and a pulse rate digital watch thermometer. The blood pressure field 306 may illustrate reading 100/80 mm/Hg for blood pressure device connected to the host processing system 100. The sugar level field 308 may illustrate reading 95 mg/dl for the glucose meter connected to the host processing system 100. The pulse rate/heart condition field 310 may illustrate reading 80 BPM and 75 BPM for pulse reader device and the pulse rate digital watch respectively connected to the host processing system 100. The pulse rate/ heart condition field 310 may also illustrates normal heart condition for ECG device. The temperature field 312 may illustrate temperature reading 98° F. for digital watch thermometer connected to the host processing system 100. The oxygen level in blood field 314 may illustrate reading "HIGH" for oximeter connected to the host processing system 100.

FIG. 4 is a user interface view 450 of an illustrating a medical device (e.g., the medical device 108A and medical device 108B of FIG. 1) operating system running on a host processing system 100 with other applications optimized for the medical device (e.g., the medical device 108A and medical device 108B of FIG. 1), according to one embodiment. Particularly, FIG. 4 illustrates a display 402, readings 404, active connected devices 406, output devices 408, and tasks 410, according to one embodiment.

The display 402 may display the diagnostic information having images (e.g., ECG readings, etc.) of the patient 110A-B. The patient readings 404 may display readings of the state of the patient 110A-B (e.g., BP reading 140/90 mmHg, etc.). The active connected devices 406 may display the active medical components (e.g., the host powered medical components 102, the self powered medical component 104) connected to the host processing system 100. The output devices 408 may display the output device connected to the host processing system 100 (e.g., ECG printer, X-Ray output). The tasks 410 may display a set of applications for automated tasks (e.g., prepare report, print status, etc.).

In example embodiment, FIG. 4 illustrates the display 402, the readings 404 the active connected devices 406, the output devices 408, and the tasks 410. The display 402 to display diagnostic images, the readings 404 may display reading like 140/90 for BP, etc. The active connected devices 406 may display devices like ECG, pulse monitor, oximeter connected to the host processing system 100. The output device 408 may display printer, wireless device, etc. The tasks 410 may display automated tasks such as prepare report, print status etc.

In one embodiment, the medical operating system may be shared among the medical components (e.g., the host powered medical component 102 and the self powered medical component 104) each one may provide a different patient reading 404 to the host processing system 100. The medical component may be a self-powered medical component (e.g., the self powered medical component 104 of FIG. 1) that may have independent imaging and processing capability that preprocesses a data associated with a patient (e.g., the patient 110A-B of FIG. 1) prior to communicating the data to the host processing system 100.

Figure 5:
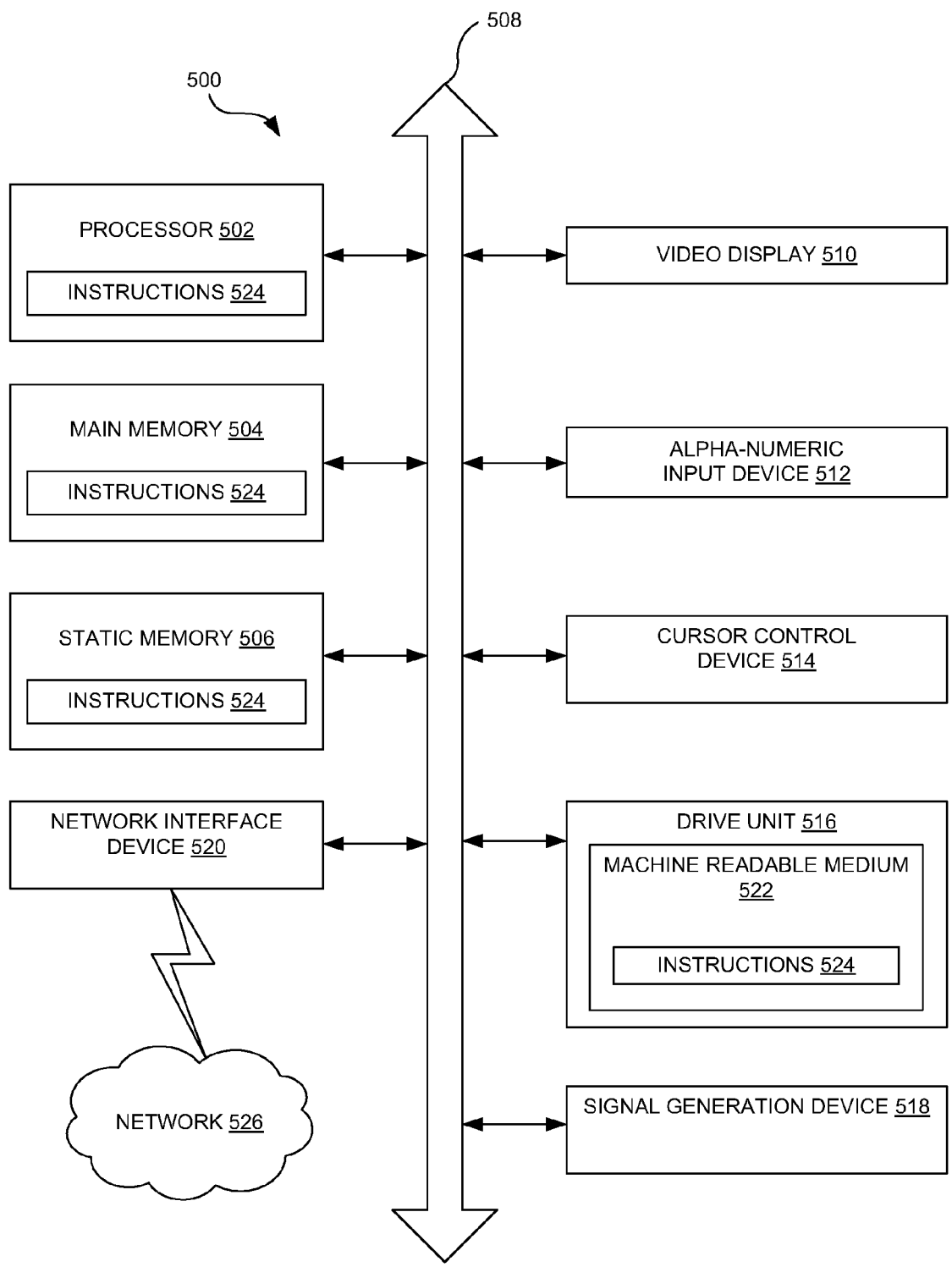
FIG. 5 is a diagrammatic system view of a data processing system in which any of the embodiments disclosed herein may be performed, according to one embodiment.

FIG. 5 is a diagrammatic system view of a data processing system in which any of the embodiments disclosed herein may be performed, according to one embodiment. Particularly, the diagrammatic system view 500 of FIG. 5 illustrates a processor 502, a main memory 504, a static memory 506, a bus 508, a video display 510, an alpha-numeric input device 512, a cursor control device 514, a drive unit 516, a signal generation device 518, a network interface device 520, a machine readable medium 522, instructions 524, and a network 526, according to one embodiment.

The diagrammatic system view 500 may indicate a personal computer and/or the data processing system in which one or more operations disclosed herein are performed. The processor 502 may be a microprocessor, a state machine, an application specific integrated circuit, a field programmable gate array, etc. (e.g., Intel® Pentium® processor). The main memory 504 may be a dynamic random access memory and/ or a primary memory of a computer system.

The static memory 506 may be a hard drive, a flash drive, and/or other memory information associated with the data processing system. The bus 508 may be an interconnection between various circuits and/or structures of the data processing system. The video display 510 may provide graphical representation of information on the data processing system. The alpha-numeric input device 512 may be a keypad, a keyboard and/or any other input device of text (e.g., a special device to aid the physically handicapped).

The cursor control device 514 may be a pointing device such as a mouse. The drive unit 516 may be the hard drive, a storage system, and/or other longer term storage subsystem. The signal generation device 518 may be a bios and/or a functional operating system of the data processing system. The network interface device 520 may be a device that performs interface functions such as code conversion, protocol conversion and/or buffering required for communication to and from the network 526. The machine readable medium 522 may provide instructions on which any of the methods disclosed herein may be performed. The instructions 524 may provide source code and/or data code to the processor 502 to enable any one or more operations disclosed herein.

Figure 6A:
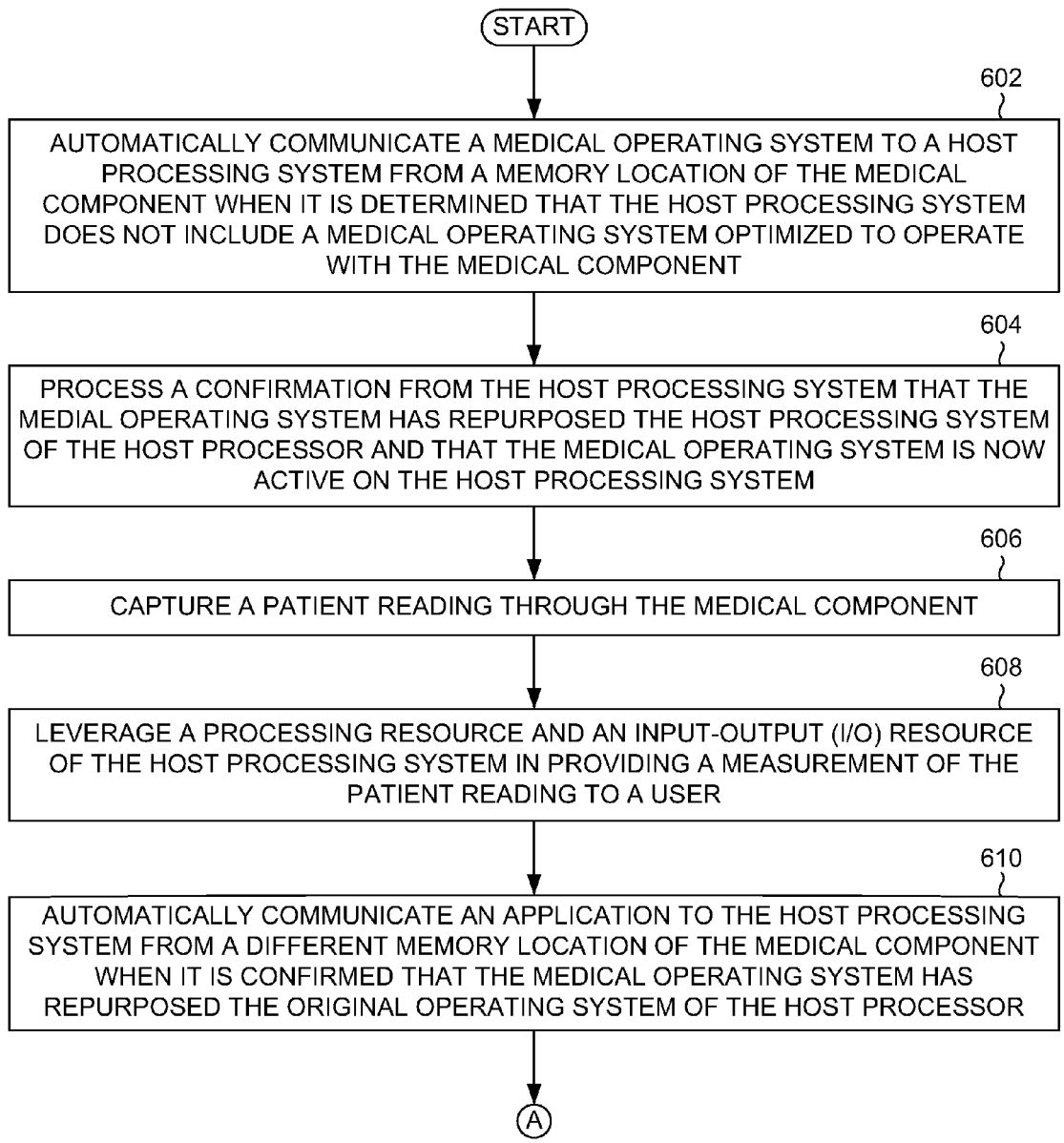
FIG. 6A is a process flow of automatically communicating an application to a host processing system from a memory location of a medical component, according to one embodiment.

FIG. 6A is a process flow of automatically communicating an application (e.g., using an application module 212 of FIG. 2) to a host processing system (e.g., the host processing system 100 of FIG. 1) from a memory location of the medical component (e.g., the host powered medical component 102, and the self powered medical component 104 of FIG. 1), according to one embodiment. In operation 602, a medical operating system may be communicated automatically (e.g., using the repurpose module 106A and the repurpose module 106B of FIG. 1) to a host processing system 100 from a memory location (e.g., from the memory device 210 of FIG. 2) of the medical component 102 and 104 when it is determined that the host processing system 100 does not include a medical operating system optimized to operate with the medical component 102 and 104. In operation 604, a confirmation may be processed from the host processing system 100 that the medial operating system has repurposed the host processing system 100 of the host processor and that the medical operating system is now active on the host processing system 100 (e.g., using the repurpose module 106A-B of FIG. 1). In operation 606, a patient reading (e.g., the patient reading 404 of FIG. 4) may be captured through the medical component 102 and 104 (e.g., using the processor module 124 of FIG. 1).

In operation 608, a processing resource and an input-output (I/O) resource of the host processing system 100 may be leveraged in providing a measurement of the patient reading (e.g., using the processor module 124 of FIG. 1) to a user (e.g., the user 112 of FIG. 1). In operation 610, an application may be communicated automatically to the host processing system 100 from a different memory location of the medical component 102 and 104 when it may be confirmed that the medical operating system has the host processing system 100 (e.g., using the communication module 208 of FIG. 1).

Figure 6B:
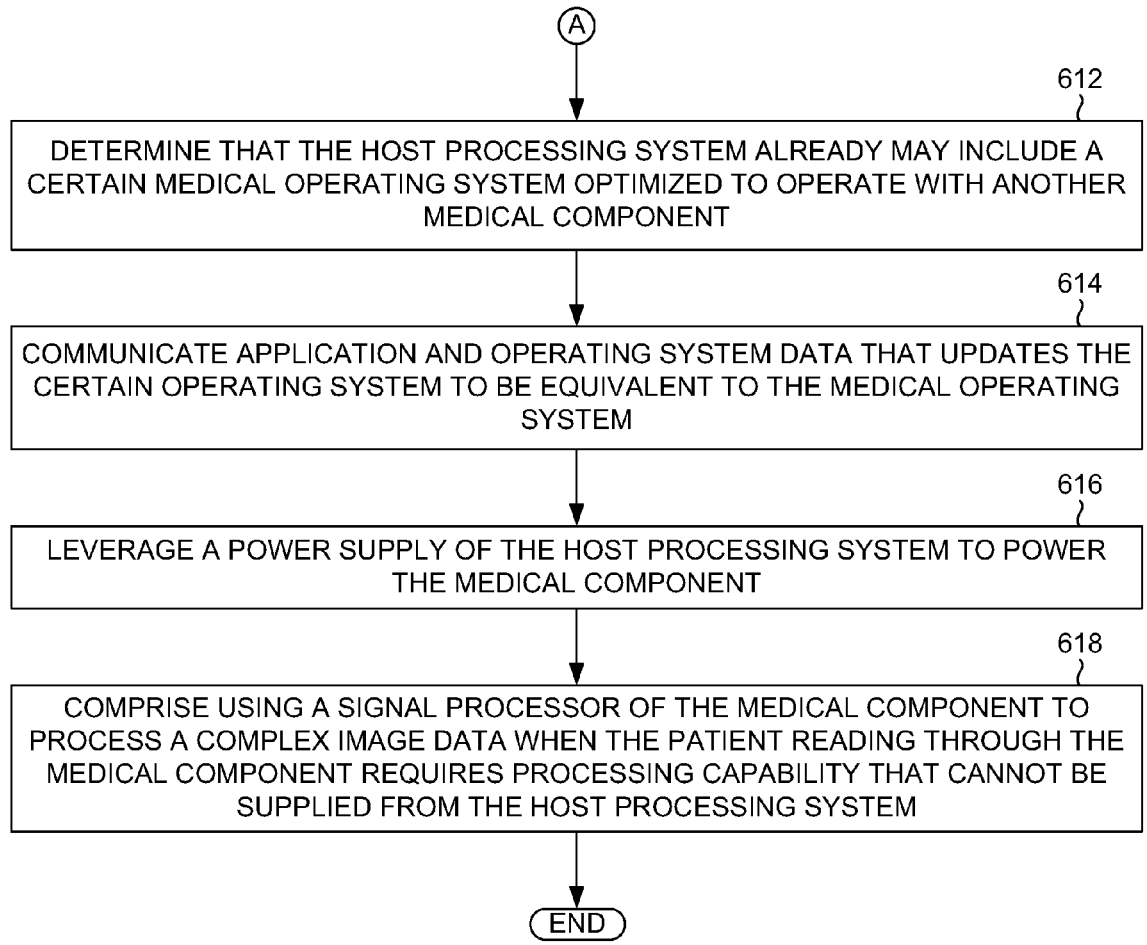
FIG. 6B is a continuation of process flow of FIG. 6A, illustrating additional processes, according to one embodiment.

FIG. 6B is a continuation of process flow of FIG. 6A, illustrating additional processes, according to one embodiment. In operation 612, it may be determined that the host processing system 100 may already include a certain medical operating system optimized to operate with another medical component 102 and 104. In operation 614, the application and operating system data may be communicated that updates the certain operating system to be equivalent to the medical operating system (e.g., using the communication module 208 of FIG. 2). In operation 616, a power supply (e.g., the power supply 120 of FIG. 1) of the host processing system 100 may be leveraged to power the medical component 104. In operation 618, a signal processor of the medical component 102 and 104 may be used to process a complex data when the patient reading 404 through the medical component 102 and 104 requires processing capability (e.g., using the processor module 204 of FIG. 2) that cannot be supplied from the host processing system 100 (e.g., using the processor module 204 of FIG. 2).

Figure 7A:
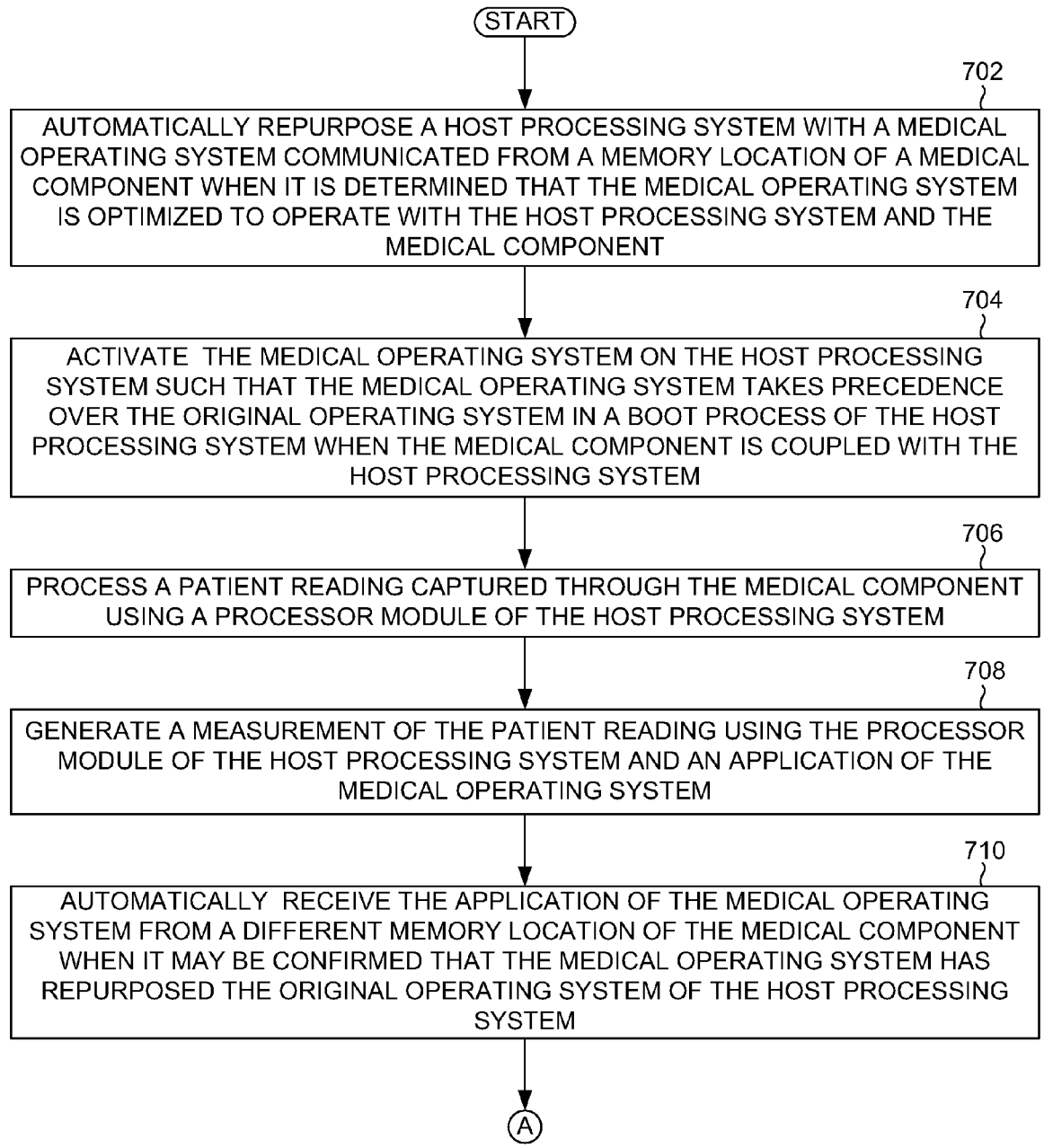
FIG. 7A is a process flow of receiving a medical operating system from a memory location of a medical component to a host processing system, according to one embodiment.

FIG. 7A is a process flow of processing a patient reading (e.g., the patient reading 404 of FIG. 4) captured through the medical component (e.g., the host powered medical component 102 and the self powered medical component 104 of FIG. 1) using a processor module (e.g., the processor module 204 of FIG. 2) of a host processing system (e.g., the host processing system 100 of FIG. 1), according to one embodiment. In operation 702, a medical operating system may be automatically repurposed with a medical operating system communicated from a memory location (e.g., the memory device 210 of FIG. 2) of the medical component 102 and 104 when it may be determined that the medical operating system is optimized to operate with the host processing system 100 and the medical component 102 and 104 (e.g., using the repurpose module 106A-B of FIG. 1).

In operation 704, the medical operating system may be activated on the host processing system 100 such that the medical operating system takes precedence over the host processing system 100 in a boot process of the host processing system 100 when the medical component 102 and 104 is coupled with the host processing system 100 (using the processor module 124 of FIG. 1). In operation 706, a patient reading (e.g., the patient reading 404 of FIG. 4) captured may be processed through the medical component 102 and 104 using a processor module 124 of the host processing system 100. In operation 708, a measurement of the patient reading 404 may be generated using the processor module 124 of the host processing system 100 and an application of the medical operating system. In operation 710, the application of the medical operating system may be received automatically from a different memory location of the medical component 102 and 104 (e.g., using the application module 212 of FIG. 2) when it may be confirmed that the medical operating system has repurposed the host processing system 100 to operate with the medical component 102 and 104.

Figure 7B:
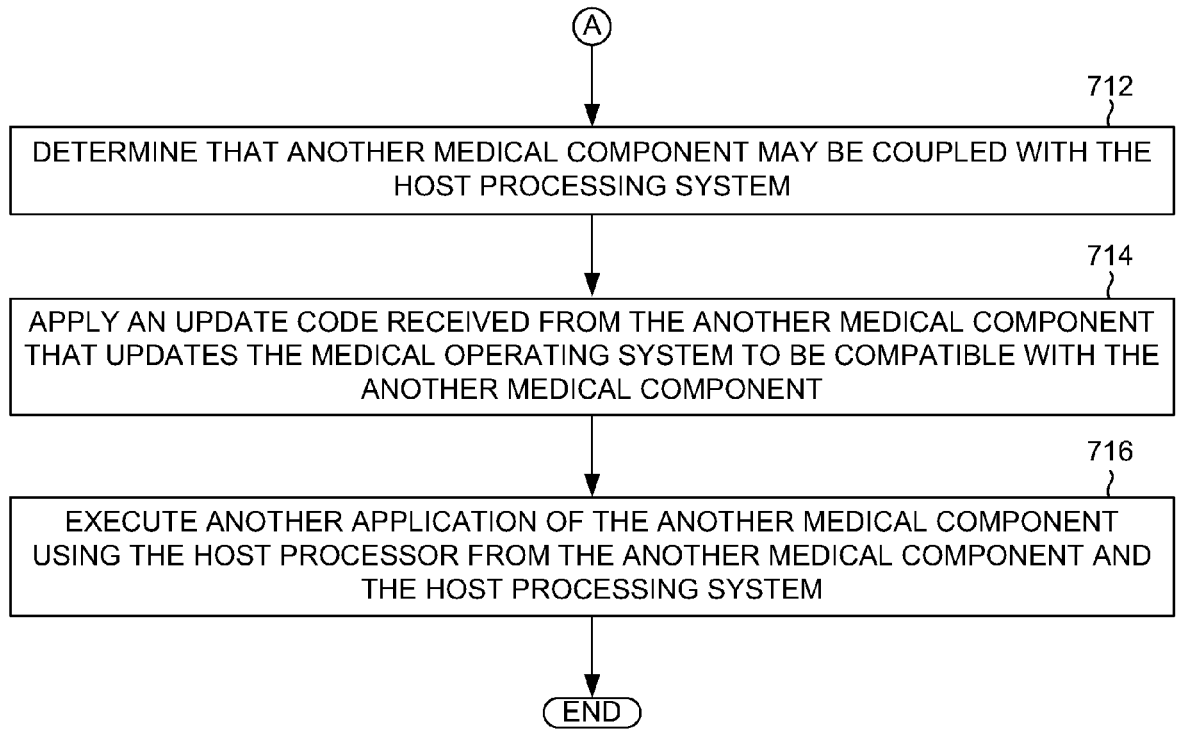
FIG. 7B is a continuation of process flow of FIG. 7A, illustrating additional processes, according to one embodiment.

FIG. 7B is a continuation of process flow of FIG. 7A, illustrating additional processes, according to one embodiment. In operation 712, it may be determined that another medical component 102 and/or 104 is coupled with the host processing system 100 (e.g., using the processor module 124 of FIG. 1). In operation 714, an update code received may be applied from the another medical component 102 and/or 104 that may update the medical operating system to be compatible with the another medical component 102 and/or 104. In operation 716, another application of the another medical component 102 and/or 104 may be executed using the host processor (e.g., using the processor module 204 of FIG. 2) from the another medical component 102 and/or 104 and the host processing system 100.

Although the present embodiments have been described with reference to specific example embodiments, it will be evident that various modifications and changes may be made to these embodiments without departing from the broader spirit and scope of the various embodiments.

Particularly, the repurpose module 106A-B and processor module 124 of FIG. 1, and the processor module 204, the operation system module 206, the communication module 208, the application module 212 and the signal processing module 214 of FIG. 1-7B, may be enabled using software and/or using transistors, logic gates, and electrical circuits (e.g., application specific integrated ASIC circuitry) such as a repurpose circuits, and a processor circuit, an operation system circuit, a communication circuit, an application circuit, an signal processor circuit, and other circuits using one or more of the technologies described herein.

In addition, it will be appreciated that the various operations, processes, and methods disclosed herein may be embodied in a machine-readable medium and/or a machine accessible medium compatible with a data processing system (e.g., a computer system), and may be performed in any order (e.g., including using means for achieving the various operations). Accordingly, the specification and drawings are to be regarded in an illustrative rather than a restrictive sense.

What is claimed is:

1. A method of using a medical component for diagnosing a patient, the method comprising:
   automatically communicating a medical operating system to a host processing system from a memory location of the medical component when it is determined that the host processing system does not include a medical operating system optimized to operate with the medical component, the medical operating system taking precedence over a host operating system of the host processing system in a boot process of the host processor when the medical component is coupled to the host processor;
   processing a confirmation from the host processing system that the medical operating system has repurposed the host processing system and that the medical operating system is now active on the host processing system;
   automatically communicating an application to the host processing system from a different memory location of the medical component when the host processing system confirms that the medical operating system has repurposed the host processing system;
   capturing a patient reading through the medical component, wherein the patient reading comprises a photoplethysmograph of a pulse oximeter that indirectly measures oxygen saturation of blood of a patient and changes in blood volume in a skin of the patient; and
   leveraging a power supply of the host processing system to power the medical component and at least one of a processing resource and an input-output (I/O) resource of the host processing system to run the application in providing a measurement of the patient reading to a user.

2. The method of claim 1 further comprising:
determining that the host processing system already includes a certain medical operating system optimized to operate with another medical component; and
communicating only application and operating system data that updates the certain operating system to be equivalent to the medical operating system.

3. The method of claim 1 wherein the patient reading is an electrocardiogram that records an electrical activity of a heart of a patient over time.

4. The method of claim 1 wherein the medical operating system is common to the medical component and other medical components, such that when other medical components are coupled with the host processing system, the medical operating system of the host processing system does not need to be reinstalled.

5. The method of claim 1 wherein the medical component is coupled with the host processing system through a standard interface.

6. The method of claim 5 wherein the standard interface is a Universal Serial Bus (USB) interface.

7. The method of claim 1 wherein the processing resource is a microprocessor of the host processing system and wherein the I/O resource of the host processing system is at least one of a printing device, a display device, an input device, and a network communication resource.

8. The method of claim 1 further comprising using a signal processor of the medical component to process a complex data when the patient reading through the medical component requires processing capability that cannot be supplied from the host processing system.

9. The method of claim 1 in a form of a machine-readable medium embodying a set of instructions that, when executed by a machine, causes the machine to perform the method of claim 1.

10. A method of using a host processing system for diagnosing a patient, the method comprising:
automatically repurposing the host processing system with a medical operating system communicated from a memory location of a medical component when it is determined that the medical operating system is optimized to operate with the host processing system and the medical component;
activating the medical operating system on the host processing system such that the medical operating system takes precedence over the original operating system in a boot process of the host processing system when the medical component is coupled with the host processing system;
automatically receiving an application of the medical operating system from a different memory location of the medical component when the host processing system confirms that the medical operating system has repurposed the host processing system to operate with the medical component;
processing a patient reading captured through the medical component using a processor module of the host processing system; and
generating a measurement of the patient reading using the processor module of the host processing system and the application of the medical operating system.

11. The method of claim 10 further comprising:
determining that another medical component is coupled with the host processing system; and
applying an update code received from the another medical component that updates the medical operating system to be compatible with the another medical component; and
executing another application of the another medical component using the host processor from at least one of the another medical component and the host processing system.

12. The method of claim 10 wherein the medical operating system of the host processing system does not need to be reinstalled even when other medical components are coupled with the host processing system.

13. A system comprising:
a medical component to capture a patient reading and to provide a medical operating system optimized for the medical component; and
a host processing system to couple with the medical component through a standard interface of the host processing system, and to replace an original operating system of the host processing system with that of the medical operating system when the medical component is coupled with the host processing system;
the medical component being configured to automatically communicate the medical operating system to the host processing system when the host processing system is coupled with the medical component so that the medical operating system takes precedence over the original operating system in a boot process of the host processing system, and so that the host processing system transmits a confirmation to the medical component that the medical operating system has repurposed the host processing system and that the medical operating system is now active on the host processing system, wherein the medical component automatically communicates an application to the host processing system when the host processing system confirms that the medical operating system has repurposed the host processing system;
the medical component configured to capture patient data and to leverage at least one of a processing resource and an input-output (I/O) resource of the host processing system so as to provide a measurement of the patient reading to a user using the application.

14. The system of claim 13, wherein the medical operating system is shared among a plurality of medical components each providing a different patient reading to the host processing system.

15. The system of claim 13 wherein the standard interface is a Universal Serial Bus (USB) interface.

16. The system of claim 13 wherein the medical component is a self-powered medical component that has independent imaging, I/O, and processing capability that preprocesses a data associated with a patient prior to communicating the data to the host processing system.

\* \* \* \* \*